United States Patent [19]

Kai et al.

[11] Patent Number: 5,578,387
[45] Date of Patent: Nov. 26, 1996

[54] FLUORINE-CONTAINING ALKYLSUCCINIC ACID DIESTER, PROCESS FOR PREPARING THE SAME AND USE THEREOF

[75] Inventors: Yoshiaki Kai, Neyagawa; Naoko Mizuno, Hirakata, both of Japan

[73] Assignee: Matsushita Electric Industrial Co., Ltd., Osaka, Japan

[21] Appl. No.: 333,296

[22] Filed: Nov. 1, 1994

Related U.S. Application Data

[62] Division of Ser. No. 38,263, Mar. 29, 1993, Pat. No. 5,391,814.

[30] Foreign Application Priority Data

Mar. 31, 1992 [JP] Japan ............................. 4-76692

[51] Int. Cl.$^6$ ......................................... G11B 5/66
[52] U.S. Cl. ........................ 428/694 T; 428/694 TP; 428/694 TF; 428/695; 428/900
[58] Field of Search ................... 428/694 T, 694 TP, 428/694 TF, 695, 900

[56] References Cited

U.S. PATENT DOCUMENTS

| | | | |
|---|---|---|---|
| 2,294,259 | 8/1942 | van Peski et al. | 560/198 |
| 3,096,363 | 7/1963 | Ballard et al. | 560/122 |
| 3,219,687 | 11/1965 | Zisman et al. | 560/197 |
| 3,856,849 | 12/1974 | Huber-Emden et al. | 560/220 |
| 3,890,376 | 6/1975 | Jäger | 560/197 |
| 4,340,749 | 7/1982 | Patel | 560/182 |
| 4,473,371 | 9/1984 | Schinzel et al. | 8/115.62 |
| 5,066,539 | 11/1991 | Inoue et al. | 428/328 |
| 5,091,243 | 2/1992 | Nishikawa | 428/336 |
| 5,094,898 | 3/1992 | Morita | 428/65.4 |
| 5,118,565 | 6/1992 | Suzuki | 428/336 |
| 5,128,216 | 7/1992 | Ng | 428/694 BP |
| 5,188,747 | 2/1993 | Kai | 252/54 |
| 5,198,136 | 3/1993 | Totemoto | 252/54 |
| 5,252,400 | 10/1993 | Mizuno | 428/421 |
| 5,374,480 | 12/1994 | Nishikawa | 428/336 |
| 5,391,814 | 2/1995 | Kai | 560/197 |

FOREIGN PATENT DOCUMENTS

| | | |
|---|---|---|
| 0473871 | 3/1992 | European Pat. Off. . |
| 58-41438 | 3/1983 | Japan . |
| 59-127230 | 7/1984 | Japan . |
| 62-58424 | 3/1987 | Japan . |
| 2-49218 | 2/1990 | Japan . |
| 3-61251 | 9/1991 | Japan . |

*Primary Examiner*—Leszek Kiliman
*Attorney, Agent, or Firm*—Wenderoth, Lind & Ponack

[57] ABSTRACT

A magnetic recording medium comprising a lubricating layer comprising a fluorine-containing alkylsuccinic acid diester of the formula:

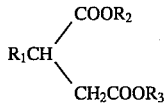

wherein $R_1$ is an aliphatic alkyl or alkenyl group, and one of $R_2$ and $R_3$ is a fluoroalkylether group and the other is a fluoroalkyl group, a fluoroalkenyl group, a fluorophenyl group, an aliphatic alkyl group or an aliphatic alkenyl group, which has excellent lubricity in an atmosphere having low to high humidity.

3 Claims, No Drawings

FLUORINE-CONTAINING ALKYLSUCCINIC ACID DIESTER, PROCESS FOR PREPARING THE SAME AND USE THEREOF

This application is a division of U.S. patent application Ser. No. 08/038,263, filed Mar. 29, 1993 (now U.S. Pat. No. 5,391,814).

BACKGROUND OF THE INVENTION

1. Field of the Invention

The present invention relates to a fluorine-containing alkylsuccinic acid diester which is useful as a lubricant for a precision instrument or part with which highly precise lubrication is required, a surfactant, a mold release agent, or a rust preventive, a process for preparing said diester and a magnetic recording medium which has a lubricating layer comprising said diester.

2. Description of the Related Art

With miniaturization and tendency for high accuracy of a machine or apparatus or a part, a lubricating type of a sliding part thereof has been shifted from fluid lubrication to boundary lubrication. In particular, with electronic equipments or parts such as a VTR, a magnetic disc and the like, a ferromagnetic metal thin film is used for the increase of a recording density. Then, highly accurate lubrication is required for sliding contact of a magnetic tape or disc against a magnetic head. For example, in the case of a metal deposition tape or hard disc, a lubricant layer is formed on a magnetic layer in a thickness of only several ten Å to reduce a spacing loss between the magnetic recording medium and the magnetic head as much as possible and to achieve a large output, while maintaining durability and reliability of the tape or disc. To this end, it is highly desired to develop an organic compound having good lubricity as a material for forming such lubricant layer.

As a lubricant for a metal thin film type magnetic recording medium, a fluoroalkylether group-containing monocarboxylic acid of the formula:

$$R_4COOH \quad (1)$$

wherein $R_4$ is a fluoroalkylether group has been proposed since it has good compatibility with the metal thin film (see Japanese Patent Kokai Publication Nos. 41438/1983, 127230/1984 and 58414/1987).

Recently, a perfluoropolyether ester of a monocarboxylic acid of the formula:

$$R_5—(OOCR_6)_n \quad (2)$$

wherein $R_5$ is a perfluoroalkylpolyether group, $R_6$ is an aliphatic alkyl group and n is a number of 1 to 6 has been proposed as a lubricant (see Japanese Patent Kokai Publication No. 49218/1990).

However, the lubricant comprising the fluoroalkylether group-containing monocarboxylic acid (1) or the perfluoropolyether ester of monocarboxylic acid (2) will lose its lubricity in a high humidity atmosphere.

SUMMARY OF THE INVENTION

One object of the present invention is to provide a novel fluorine-containing alkylsuccinic acid diester which is useful as a lubricant suffering from no or less deterioration of lubricity in an atmosphere of from low humidity to high humidity.

Another object of the present invention is to provide a process for preparing the novel fluorine-containing alkylsuccinic acid diester of the present invention.

A further object of the present invention is to provide a magnetic recording medium having a lubricating layer which contains the novel fluorine-containing alkylsuccinic acid diester of the present invention as a lubricant.

According to a first aspect of the present invention, there is provided a fluorine-containing alkylsuccinic acid diester of the formula:

$$R_1CH\begin{matrix}COOR_2\\ \\CH_2COOR_3\end{matrix} \quad (I)$$

wherein $R_1$ is an aliphatic alkyl or alkenyl group, and one of $R_2$ and $R_3$ is a fluoroalkylether group and the other is a fluoroalkyl group, a fluoroalkenyl group, a fluorophenyl group, an aliphatic alkyl group or an aliphatic alkenyl group.

According to a second aspect of the present invention, there is provided a magnetic recording medium comprising a nonmagnetic substrate, a ferromagnetic metal layer formed thereon and a lubricating layer comprising a fluorine-containing alkylsuccinic acid diester of the formula (I). The magnetic recording medium may optionally have a protective layer between the ferromagnetic metal layer and the lubricating layer.

According to a third aspect of the present invention, there is provided a process (first process) for preparing a fluorine-containing alkylsuccinic acid diester of the formula (I) comprising the steps of addition reacting an aliphatic alkylsuccinic anhydride or aliphatic alkenylsuccinic anhydride with a fluoroalkylether group-containing alcohol in the presence of an acid catalyst to obtain a monoester and esterifying said monoester with at least one compound selected from the group consisting of a fluoroalkyl group-containing alcohol, a fluoroalkenyl group-containing alcohol, a fluorophenyl group-containing alcohol, an aliphatic alkyl alcohol and an aliphatic alkenyl alcohol in the presence of an acid catalyst to obtain the diester.

According to a fourth aspect of the present invention, there is provided a process (second process) for preparing a fluorine-containing alkylsuccinic acid diester of the formula (I) comprising the steps of addition reacting an aliphatic alkylsuccinic anhydride or aliphatic alkenylsuccinic anhydride with at least one compound selected from the group consisting of a fluoroalkyl group-containing alcohol, a fluoroalkenyl group-containing alcohol, a fluorophenyl group-containing alcohol, an aliphatic alkyl alcohol and an aliphatic alkenyl alcohol to obtain a monoester and esterifying said monoester with a fluoroalkylether group-containing alcohol in the presence of an acid catalyst to obtain the diester.

According to a fifth aspect of the present invention, there is provided a process (third process) for preparing a fluorine-containing alkylsuccinic acid diester of the formula (I) comprising the steps of addition reacting an aliphatic alkylsuccinic anhydride or aliphatic alkenylsuccinic anhydride with a fluoroalkylether group-containing alcohol in the presence of an acid catalyst to obtain a monoester, chlorinating said monoester to obtain a chlorinated carboxylic acid and reacting said chlorinated carboxylic acid with at least one compound selected from the group consisting of a fluoroalkyl group-containing alcohol, a fluoroalkenyl group-containing alcohol, a fluorophenyl group-containing alcohol, an aliphatic alkyl alcohol and an aliphatic alkenyl alcohol in the presence of a base catalyst.

According to a sixth aspect of the present invention, there is provided a process (fourth process) for preparing a fluorine-containing alkylsuccinic acid diester of the formula (I) comprising the steps of addition reacting an aliphatic alkylsuccinic anhydride or aliphatic alkenylsuccinic anhydride with at least one compound selected from the group consisting of a fluoroalkyl group-containing alcohol, a fluoroalkenyl group-containing alcohol, a fluorophenyl group-containing alcohol, an aliphatic alkyl alcohol and an aliphatic alkenyl alcohol to obtain a monoester, chlorinating said monoester to obtain a chlorinated carboxylic acid and reacting said chlorinated carboxylic acid with a fluoroalkylether group-containing alcohol in the presence of a base catalyst to obtain the diester.

DETAILED DESCRIPTION OF THE INVENTION

The aliphatic alkyl or alkenyl group for substituent $R_1$ in the formula (I) has preferably 6 to 30 carbon atoms, more preferably 10 to 24 carbon atoms. When the number of carbon atoms in the aliphatic alkyl or alkenyl group is less than 6 or larger than 30, the diester may have decreased lubricity.

The fluoroalkylether group for the substituent $R_2$ or $R_3$ has preferably 5 to 50 carbon atoms, more preferably 8 to 30 carbon atoms. The fluoroalkyl ether group has at least one fluorine atom and it can be a perfluoroalkylether group. When the number of carbon atoms in the fluoroalkylether group is less than 5 or larger than 50, the diester may have deteriorated lubricity.

The fluoroalkyl or fluoroalkenyl group or the aliphatic alkyl or alkenyl group has preferably 30 or less carbon atoms, more preferably 20 or less carbon atoms. When the number of carbon atoms exceeds 30, the diester may have deteriorated lubricity. The fluorophenyl group may contain 1 to 5 fluorine atoms.

The fluorine-containing alkylsuccinic acid diester of the present invention is preferably prepared by either one of the processes of the present invention.

In the first and second processes, the addition reaction for the preparation of monoester and the esterification for the preparation of diester are carried out in the presence of a hydrophobic solvent in which the reactants and the monoester are dissolved and in which the reaction temperature is in a range between 40° C. and 150° C., preferably 60° C. and 120° C. except alcohols or esters. Specific examples of such solvent are n-heptane, benzene, toluene, isooctane, cyclohexane, ethylene chloride, isopropyl ether, etc.

As the acid catalyst, any acid catalyst which can be used in a conventional esterification may be used. Examples of the acid catalyst are inorganic acids (e.g. sulfuric acid, hydrochloric acid, etc.), organic acids (e.g. aromatic sulfonic acids, etc.) and Lewis acids (e.g. boron fluoride etherate, etc.).

In the first process, the acid catalyst is used in an amount of 2 to 10% by weight based on the total weight of the aliphatic alkyl- or alkenylsuccinic anhydride and the fluoroalkyl group-containing alcohol in the preparation of monoester, and 1 to 3% by weight based on the total weight of the monoester and the alcohol is used in the preparation of diester.

In the second process, the acid catalyst is used in an amount of 2 to 10% by weight based on the total weight of the monoester and the fluoroalkylether group-containing alcohol.

In the first process, a molar ratio of the aliphatic alkyl- or alkenylsuccinic anhydride to the fluoroalkylether group-containing alcohol is preferably from 2:1 to 1:2, more preferably from 3:2 to 2:3. The molar ratio of the monoester to at least one compound selected from the group consisting of a fluoroalkyl group-containing alcohol, a fluoroalkenyl group-containing alcohol, a fluorophenyl group-containing alcohol, an aliphatic alkyl alcohol and an aliphatic alkenyl alcohol is preferably from 2:1 to 1:2, more preferably from 3:2 to 2:3.

The above molar ratios can apply to molar ratios in the second process.

In the third and fourth processes, the same solvent as used in the above processes may be used. Also, the same catalyst as used in the above processes may be used in the same amount.

In the chlorination step, the monoester is chlorinated with a chlorinating agent such as phosphoryl chloride, thionyl chloride, phosphorus pentachloride, phosphorus trichloride, etc.

The chlorination agent is used in an amount of 3 to 30 equivalents per one mole of the monoester.

The chlorination of monoester can be carried out in a liquid phase in the presence or absence of a solvent at a temperature of 10° C. to a refluxing temperature of the reaction mixture. When the solvent is used, n-hexane, cyclohexane, benzene, chloroform, ethyl ether, and the like may be used.

As the base catalyst, any base catalyst which can be used in a conventional esterification may be used. Examples of the base catalyst are pyridine, triethylamine, zinc chloride, iodide and the like.

The base catalyst is used in an amount of 10 to 100% by weight of the chlorinated carboxylic acid.

The molar ratios between the reagents in the third and fourth processes are analogous to those in the first and second processes.

The magnetic recording medium can be produced by any of the conventional methods using the diester of the present invention as a lubricant. For example, a ferromagnetic layer is formed on a non-magnetic substrate by a known method such as sputtering. Then, a lubricating layer comprising the diester of the present invention is coated on the ferromagnetic layer with or without a protective layer between the ferromagnetic layer and the lubricating layer.

In addition to the diester of the present invention, the lubricating layer may optionally contain one or more known additives such as other lubricant, a rust preventive, etc.

The diester of the present invention is coated on the ferromagnetic layer in an amount of 0.05 to 100 $mg/m^2$, preferably 0.1 to 50 $mg/m^2$.

As the other lubricant and the rust preventive, fluorine-containing ones are preferred. In particular, liquid fluorine-containing compounds are preferred.

The amount of the other lubricant and/or the rust preventive is from 0 to 80% by weight, preferably 0 to 70% by weight of the total weight of the lubricating layer.

When the amount of the diester of the present invention is less than 20% by weight, the effects of the present invention may not be achieved.

As the optionally formed protective layer, a carbonaceous layer is preferably used. The carbonaceous layer may be an amorphous, graphite or diamond-like carbon film or their laminated or mixed state formed by sputtering, plasma CVD and the like. A thickness of the protective layer is usually from 50 to 500 Å.

The fluorine-containing alkylsuccinic acid diester of the formula (I) of the present invention contains one fluoroalkylether group and two aliphatic hydrocarbon end groups, namely the aliphatic alkyl or alkenyl end groups in a molecule, or one fluoroalkylether group, one fluorocarbon end group, namely one fluoroalkyl or fluoroalkenyl end group, and one aliphatic hydrocarbon end group in a molecule. Then, the fluoroalkylether group and the fluorocarbon group are exposed on the surface of ferromagnetic metal layer or protective layer so that they contribute to the decrease of the surface energy of such layer and provide a non-adhesive surface. Thereby, the fluoroalkylether group and the fluorocarbon group have protective functions of the surface of ferromagnetic metal layer or the magnetic head surface in a low humidity atmosphere. The fluoroalkylether group is better in this function than the fluorocarbon group. But, the fluoroalkylether group has a moisture-absorbing property in a high humidity atmosphere since it has plural hydrophilic ether linkages in the molecule. Since the fluorocarbon group and the aliphatic hydrocarbon group are hydrophobic, these groups contained in the same molecule will mask the hydrophilicity of the fluoroalkylether group. To make effective use of this masking effect, the fluorocarbon group and the aliphatic hydrocarbon group are bonded to the molecular end so that these groups will surround the fluoroalkylether group from both sides.

Since the aliphatic hydrocarbon group has a flexible carbon-carbon bond and its molecules are orientated by an intermolecular force among the adjacent molecules, it has a good lubricating property.

Since the fluorine-containing alkylsuccinic acid diester of the formula (I) of the present invention has the above end groups in good balance, it has a good lubricating property in any atmosphere from low humidity to high humidity.

PREFERRED EMBODIMENTS OF THE INVENTION

Example 1

In this Example, a compound of the formula:

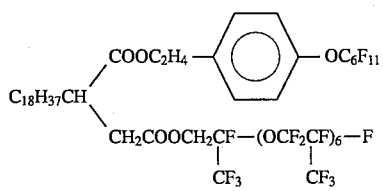

was prepared.

In a one liter flask equipped with a stirrer, octadecylsuccinic anhydride (35.3 g, 0.10 mole) of the formula:

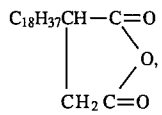

a fluoroalkylether group-containing alcohol (114.6 g, 0.10 mole) of the formula:

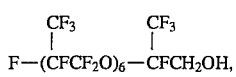

p-toluenesulfonic acid (hereinafter referred to as "PTS") (4.5 g corresponding to 3% by weight of the whole raw materials) and n-heptane (500 ml) were charged and reacted under reflux for 24 hours.

After the reaction, the reaction mixture was washed with distilled water repeatedly until the pH of the washing water decreased to 7 and was dried over anhydrous sodium sulfate. After distilling n-heptane off, the residue was dissolved in benzene and cooled to −10° C. to remove unreacted octadecylsuccinic anhydride. Then, the mixture was dissolved in methanol and cooled to −10° C. to remove the unreacted fluoroalkylether group-containing alcohol to obtain a monoester (102 g) of the formula:

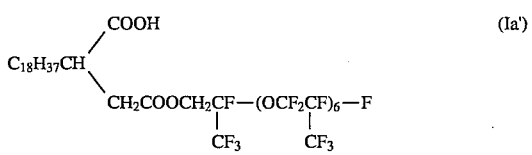

In a one liter flask equipped with a stirrer and a water condenser, the above monoester (Ia') (75.0 g, 0.05 mole), PTS (1.4 g corresponding to 1.5% by weight of the monoester), benzene (300 ml) and a fluoroalkenyl group-containing alcohol (20.9 g, 0.05 mole) of the formula:

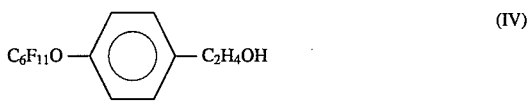

were charged and reacted under reflux for 24 hours.

After the reaction, the reaction mixture was washed with distilled water repeatedly until the pH of the washing water decreased to 7 and was dried over anhydrous sodium sulfate. After distilling benzene off, the residue was dissolved in methanol and cooled to −10° C. to remove the unreacted monoester. Then, the mixture was dissolved in isopropanol and cooled to −10° C. to remove the unreacted fluoroalkenyl group-containing alcohol to obtain a transparent colorless liquid (68 g), which was identified as the diester of the formula (Ia) containing neither raw materials nor by-products by IR, GPC and FD-MS.

IR: The peaks at 1775 $cm^{-1}$ (acid anhydride) and 3330 $cm^{-1}$ (alcohol) disappeared while the peak at 1760 $cm^{-1}$ (ester) appeared.

GPC: None of fluoroalkylether group-containing alcohol, fluoroalkenyl group-containing alcohol, octadecylsuccinic anhydride and the monoester was detected.

FD-MS: main peak at m/e of 1899.

When an aliphatic alkenylsuccinic anhydride is used in place of octadecylsuccinic anhydride in the above procedure, a corresponding diester is obtained.

When a fluoroalkyl group-containing alcohol, a fluorophenyl group-containing alcohol, an aliphatic alkyl alcohol or an aliphatic alkenyl alcohol is used in place of the fluoroalkenyl group-containing alcohol in the above procedure, a corresponding diester is obtained.

Example 2

In this Example, the diester of the formula (Ia) in Example 1 was prepared by another process.

In a one liter flask equipped with a stirrer, the octadecylsuccinic anhydride (II) (35.3 g, 0.10 mole), the fluoroalkenyl group-containing alcohol (IV) (41.8 g, 0.10 mole) and benzene (300 ml) were charged and reacted under reflux for 24 hours.

After the reaction, benzene was distilled off, and the residue was dissolved in isopropyl ether and cooled to −10° C. to remove unreacted octadecylsuccinic anhydride. Then, the mixture was dissolved in methanol and cooled to −10° C. to remove the unreacted fluoroalkenyl group-containing alcohol to obtain a monoester of the formula:

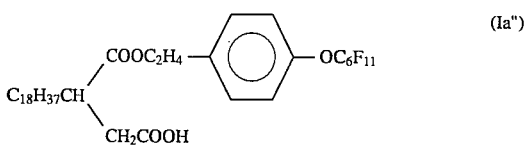
(Ia")

In a one liter flask equipped with a stirrer and a water condenser, the above monoester (Ia") (38.5 g, 0.05 mole), PTS (2.9 g corresponding to 3.0% by weight of the monoester), n-heptane (300 ml) and the fluoroalkylether group-containing alcohol (III) (57.3 g, 0.05 mole) were charged and reacted under reflux for 24 hours.

After the reaction, the reaction mixture was washed with distilled water repeatedly until the pH of the washing water decreased to 7 and was dried over anhydrous sodium sulfate. After distilling n-heptane off, the residue was dissolved in methanol and cooled to −10° C. to remove the unreacted monoester. Then, the mixture was dissolved in isopropanol and cooled to −10° C. to remove the unreacted fluoroalkylether group-containing alcohol to obtain a transparent colorless liquid (65 g), which was identified as the same diester (Ia) as obtained in Example 1.

Example 3

In this Example, the diester of the formula (Ia) in Example 1 was prepared by a further process.

In a one liter flask equipped with a stirrer, the octadecylsuccinic anhydride (II) (35.3 g, 0.10 mole), the fluoroalkylether group-containing alcohol (III) (114.6 g, 0.10 mole), PTS (4.5 g corresponding 3% by weight of of the whole raw materials) and n-heptane (500 ml) were charged and reacted under reflux for 24 hours.

After the reaction, the reaction mixture was treated in the same manner as in Example 1 to obtain the monoester (Ia') (102 g).

In a one liter flask equipped with a stirrer, the above monoester (Ia') (75.0 g, 0.05 mole) and thionyl chloride (60 g) were charged and reacted under reflux for 3 hours. After chlorination reaction, excessive thionyl chloride was distilled off under reduced pressure. To the residue, a solution of the fluoroalkenyl group-containing alcohol (IV) (20.9 g, 0.05 mole) in a mixture of pyridine (20 ml) and isopropyl ether (300 ml) was dropwise added over 2 hours while cooling with ice. After the addition of solution, the mixture was further stirred at room temperature for 4 hours to complete the reaction. Thereafter, the reaction mixture was washed with 5% hydrochloric acid (300 ml) to remove excessive pyridine from the mixture.

The reaction mixture was washed with distilled water repeatedly until the pH of the washing water decreased to 7 and dried over anhydrous sodium sulfate. After distilling isopropyl ether off, the residue was dissolved in methanol and cooled to −10° C. to remove the unreacted monoester. Then, the mixture was dissolved in isopropanol and cooled to −10° C. to remove the unreacted fluoroalkylether group-containing alcohol to obtain a transparent colorless liquid (72 g), which was identified as the same diester (Ia) as obtained in Example 1.

This process of Example 3 is characterized in that the monoester is chlorinated to obtain a chlorinated carboxylic acid and the chlorinated carboxylic acid is esterified in the presence of a base catalyst to obtain a diester. By this process, the yield reaches 90% or higher, while the yields in Examples 1 and 2 are about 70%.

In the above procedures, the fluoroalkylether group-containing alcohol was used in the monoesterifying step of the aliphatic alkylsuccinic anhydride and the fluoroalkenyl group-containing alcohol was used in the diesterifying step. These two alcohols can be used in the reverse order.

Example 4

This Example illustrates the production of a magnetic recording medium according to the present invention.

As a non-magnetic substrate, there was used a polyester film having gently sloped protrusions, which were formed by silica minute particles and had an average height of 70 Å and an average diameter of 1 µm, in a density of several protrusions per 100 µm$^2$ and sharp protrusions formed from colloidal silica particles of 150 Å in diameter as nuclei and a UV curable epoxy resin as a binder in a density of 1×10$^7$ protrusions per 1 mm$^2$ but relatively large protrusions formed by a residue of polymerization catalyst as few as possible.

On a surface of non-magnetic substrate, a Co—Ni ferromagnetic metal film having a thickness of 1000 Å and a Ni content of 20% was formed in the presence of a very small amount of oxygen by a continuous inclined vapor deposition method. An oxygen content in the ferromagnetic metal layer was 5 atomic %.

On the surface of ferromagnetic metal film, the fluorine-containing alkylsuccinic acid diester of the formula (Ia) prepared in Example 1 was coated in an amount of 10 mg/m$^2$ to form a lubricating layer.

The film was then cut to a predetermined width to obtain a magnetic tape.

The magnetic tape was repeatedly run in a commercial video deck at 23° C., 10% RH or at 40° C., 80% RH, and output characteristics were measured. The number of runs was counted until the RF output decreased by 3 dB from the original RF output or until the output started to fluctuate.

Example 5

In the same manner as in Example 4 except that the compound of the formula:

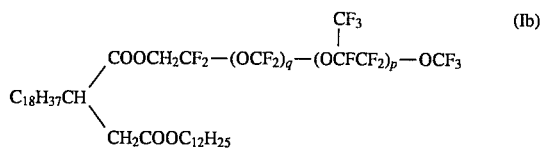
(Ib)

having a molecular weight of 2140 was used in place of the diester of the formula (Ia), a magnetic tape was produced and its property was measured.

Example 6

In the same manner as in Example 4 except that a mixture of the diester of the formula (Ia) and a commercially available lubricant of the formula:

$$C_7F_{15}C_2H_4NHC_{14}H_{29}$$

in a weight ratio of 2:1 was used in place of the diester of the formula (Ia), a magnetic tape was produced and its property was measured.

Example 7

In the same manner as in Example 4 except that a mixture of the diester of the formula (Ib) and a commercially available lubricant of the formula:

$$C_{17}H_{35}COOC_2H_4C_8F_{17}$$

in a weight ratio of 1:1 was used in place of the diester of the formula (Ia), a magnetic tape was prepared and its property was measured.

Comparative Examples 1, 2 and 3

In the same manner as in Example 4 except that a compound of the formula:

$$F-(CFCF_2O)_6-CFCOOH \quad \text{(Va)}$$
$$\phantom{F-(}|\phantom{FCF_2O)_6-}|$$
$$\phantom{F-(}CF_3\phantom{CF_2O)_6-}CF_3$$

(Comparative Example 1), a compound of the formula:

$$F-(CFCF_2O)_{14}-CFCH_2OCOC_{17}H_{35} \quad \text{(Vb)}$$
$$\phantom{F-(}|\phantom{CF_2O)_{14}-}|$$
$$\phantom{F-(}CF_3\phantom{CF_2O)_{14}-}CF_3$$

(Comparative Example 2) or a compound of the formula:

$$C_{17}H_{35}COOCH_2CF_2O(C_2F_4O)_p-$$
$$(CF_2O)_q-CF_2CH_2OCOC_{17}H_{35} \quad \text{(Vc)}$$

(Comparative Example 3) was used in place of the diester of the formula (Ia), a magnetic tape was produced and its property was measured.

The results are shown in Table 1.

TABLE 1

| Example No. | Number of Runs (times) | |
|---|---|---|
| | at 23° C., 10% RH | at 40° C., 80% RH |
| Comp. 1 | 120 | 80 |
| Comp. 2 | 130 | 110 |
| Comp. 3 | 90 | 120 |
| 4 | >200 | >200 |
| 5 | >200 | >200 |
| 6 | >200 | >200 |
| 7 | >200 | >200 |

From the results in Table 1, it is clear that the magnetic tapes having the lubricating layer comprising the fluorine-containing alkylsuccinic acid diester of the present invention had larger repeated running number in the low and high humidity than the magnetic tapes having the lubricating layer comprising the conventional lubricant.

Example 8

As a non-magnetic substrate, there was used an aluminum alloy disc having a diameter of 95 mm and a thickness of 1.2 mm which was plated with a non-magnetic Ni—P alloy of 25 μm in thickness and texture finished to form protrusions having an average surface roughness of 50 Å and the maximum height of 300 Å.

On the non-magnetic Ni—P alloy layer, a Cr primer layer having a thickness of 1300 Å and a ferromagnetic metal layer of Co—Ni having a thickness of 600 Å were formed by sputtering.

On the ferromagnetic layer, a graphite protective layer having a thickness of 200 Å was formed by sputtering (Sample A), or a diamond-like carbon protective layer having a thickness of 50 Å was formed by the plasma CVD method (Sample B).

On the protective layer of each sample, a lubricating layer was formed by coating the fluorine-containing alkylsuccinic acid diester of the formula (Ia) in an amount of 10 mg/m² to produce a magnetic disc.

The magnetic disc was subjected to the CSS (contact start and stop) test at 23° C., 10% RH or 40° C., 80% RH. The number of the CSS tests was counted until a coefficient of friction on the surface of magnetic disc exceeded 1.0 or until the head crush occurred to evaluate the durability of the magnetic disc.

Examples 9, 10 and 11

In the same manner as in Example 8 except that the diester of the formula (Ib) (Example 9), the lubricant mixture of Example 6 (Example 10) or the lubricant mixture of Example 7 (Example 11) was used in place of the diester of the formula (Ia), the magnetic disc was produced and subjected to the CSS test.

Comparative Examples 4, 5 and 6

In the same manner as in Example 8 except that, in Comparative Examples 4, 5 and 6, the same commercially available lubricants as used in Comparative Examples 1, 2 and 3 were used, respectively in place of the diester of the formula (Ia), magnetic discs were produced and subjected to the CSS test.

The results are shown in Table 2.

TABLE 2

| Example No. | Sample No. | CSS number (times) | |
|---|---|---|---|
| | | 23° C., 10% RH | 40° C., 80% RH |
| Comp. 4 | A | 18,000 | 5,000 |
| Comp. 5 | A | 20,000*) | 8,000 |
| Comp. 6 | A | 12,000*) | 10,000 |
| 8 | A | >50,000 | >50,000 |
| 9 | B | >50,000 | >50,000 |
| 10 | A | >50,000 | >50,000 |
| 11 | A | >50,000 | >50,000 |

Note: *)The head crush occurred.

From the results of Table 2, it is understood that the magnetic discs having the lubricating layer comprising the fluorine-containing alkylsuccinic acid diester of the present invention had better durability in the CSS test in the low and high humidity atmosphere than the magnetic tapes having the lubricating layer comprising the conventional lubricant.

With the following fluorine-containing alkylsuccinic acid diesters, the same results as in above Examples can be attained:

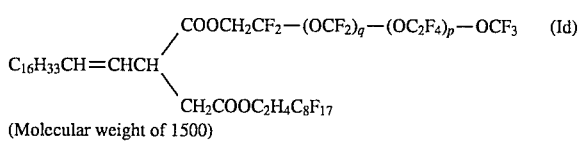
(Molecular weight of 1500) (Id)

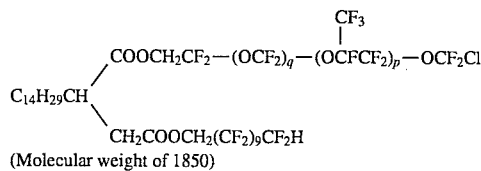
(Molecular weight of 1850) (Ie)

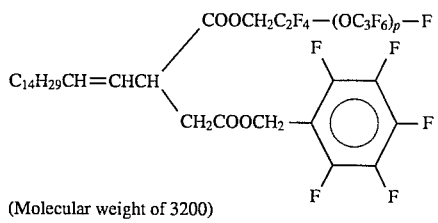
(Molecular weight of 3200) (If)

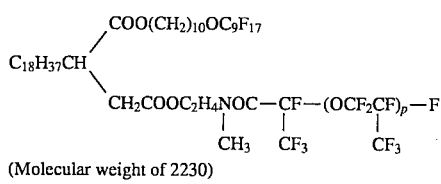
(Molecular weight of 2230) (Ig)

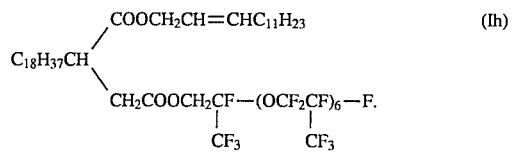
(Molecular weight of 1693) (Ih)

What is claimed is:

1. A magnetic recording medium comprising a non-magnetic substrate, a ferromagnetic metal layer formed thereon and a lubricating layer comprising a fluorine-containing alkylsuccinic acid diester of the formula

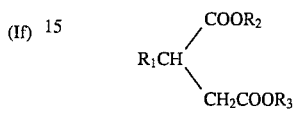

wherein $R_1$ is an aliphatic alkyl or alkenyl group each of said groups having 6 to 30 carbon atoms, one of $R_2$ and $R_3$ is a fluoroalkylether group having 5 to 50 carbon atoms and the other is a fluoroalkyl group, a fluoroalkenyl group, a fluorophenyl group, an aliphatic alkyl group or an aliphatic alkenyl group, each of said groups having 30 or less carbon atoms.

2. The magnetic recording medium according to claim 1, which further comprises a protective layer between said ferromagnetic metal layer and said lubricating layer.

3. The magnetic recording medium according to claim 1, wherein said lubricating layer further comprises another lubricant.

* * * * *